United States Patent [19]
Han et al.

[11] Patent Number: 6,090,844
[45] Date of Patent: Jul. 18, 2000

[54] PHARMACEUTICAL INJECTION SOLUTION CONTAINING TAXOL

[76] Inventors: Man Woo Han, Lotte Apt. No. 1103, 109-Dong 220-2 Nai-Dong, Suh-Ku; Jae Kuk Yoo, Kyunsung Kunmaul Apt. No. 303, 117-Dong Kalma-Dong, Suh-Ku, both of Taejeon City; Nam Doo Hong, 200-205 Sungsan-Dong, Mapo-Ku, Seoul, all of Rep. of Korea

[21] Appl. No.: 09/051,238
[22] PCT Filed: May 30, 1997
[86] PCT No.: PCT/IB97/00623
 § 371 Date: Apr. 6, 1998
 § 102(e) Date: Apr. 6, 1998
[87] PCT Pub. No.: WO98/53810
 PCT Pub. Date: Dec. 3, 1998

[30] Foreign Application Priority Data

May 28, 1996 [KR] Rep. of Korea ............... 18324

[51] Int. Cl.⁷ .................................. A61K 31/335
[52] U.S. Cl. ............................................. 514/449
[58] Field of Search ................................. 514/449

[56] References Cited

U.S. PATENT DOCUMENTS

| | | | |
|---|---|---|---|
| 5,157,049 | 10/1992 | Haugwitz et al. | 514/449 |
| 5,438,072 | 8/1995 | Bobee et al. | 514/449 |
| 5,478,860 | 12/1995 | Wheeler et al. | 514/449 |
| 5,646,176 | 7/1997 | Golik et al. | 514/449 |
| 5,795,909 | 8/1998 | Shashoua et al. | 514/449 |
| 5,922,754 | 7/1999 | Burchett et al. | 514/449 |
| 5,925,776 | 7/1999 | Nikalayev et al. | 554/319 |

*Primary Examiner*—James H. Reamer
*Attorney, Agent, or Firm*—Bachman & LaPointe, P.C.

[57] ABSTRACT

The present invention is a pharmaceutical compound which is used for the preparation of TAXOL® as an injection solution which is effective in clinical utilization as a cancer-inhibiting drug. The addition of calcium disodium edetate and tromethamine to conventional injections solutions enhances the stability of the solution and reduces the side effects normally associated with administration of TAXOL®. The compound comprises dehydrated ethanol, polyepoxilated castor oil, tromethamine, and calcium disodium edetate in specified ranges.

3 Claims, No Drawings

PHARMACEUTICAL INJECTION SOLUTION CONTAINING TAXOL

BACKGROUND OF THE INVENTION

1. Field of the Invention

The present invention relates generally to the field of pharmaceuticals, and particularly to the various pharmaceutical compositions which are used in the preparation and administration of TAXOL® and its derivatives.

2. Description of the Prior Art

TAXOL® (paclitaxel) is one of a class of drugs called taxanes. These types of drugs promote polymerization of tubulin and stabilize the structure of intracellular microtubules. This process has the effect of inhibiting the normal dynamic reorganization of the microtubules that is necessary for interphase and mitotic functions. Paclitaxel may also potentiate the cytotoxic effects of radiation.

In December of 1992, the Food and Drug Administration (FDA) approved the natural form of paclitaxel for treatment of metastatic ovarian cancer after failure of first-line or subsequent chemotherapy, and the use of paclitaxel for the treatment of metastatic breast cancer received marketing approval in April of 1994. Although paclitaxel has shown to have effects of inhibiting the progression of cancer in some patients, it has proven to be somewhat difficult to prepare and administer. Usually applied to patients intravenously, TAXOL® is diluted in a suitable parenteral fluid since it is available only in a somewhat viscous solution. Its insolubility in water makes administration of the drug somewhat difficult.

Therefore, a number of different compositions have been proposed to be used as solvents for preparing TAXOL® for injection. For Example, U.S. Pat. No. 5,478,860 discloses a manufacturing process mixing TAXOL® with olive or sunflower-seed oil and polyethyleneglycol (PEG) into a microemulsion. In addition, European Patent No. 639,577 discloses a process of manufacturing the derivatives of TAXOL® having enhanced solubility in water by way of using phosphooxymethyl (POM) or methyltheomethyl (MTM). The PCT petitioned International Publication, WO-9318757, discloses a process which solves the solubility problem and enhances the pharmaceutical stability through the development of liposome-encapsulated TAXOL® as a drug delivery system (DDS).

Presently, the most common form of solvent for preparing a TAXOL® injection solution is a mixture of dehydrated ethanol and polyepoxilated castor oil. The stability of injection solutions prepared in this manner is limited, and the use of these solutions after prolonged storage may result in the neutralization of the TAXOL® or induced side effects to the patient due to the dissociation of the TAXOL® in solution.

Therefore, there is a current need for a pharmaceutical compound which is effective in the preparation of a TAXOL® injection solution which maintains the stability of the TAXOL® in solution during prolonged storage. This is done in an effort to produce an injection solution which when administered to patients reduces the side effects normally associated with a TAXOL® injection solution prepared using previous disclosed or conventional methods.

Accordingly, the principle object of the present invention is to provide a pharmaceutical compound which is used for the preparation of TAXOL® as an injection solution.

Another object of the present invention is to provide a pharmaceutical compound which significantly reduces the side effects normally associated with the use of conventional TAXOL® injection solutions.

SUMMARY OF THE INVENTION

The present invention discloses a pharmaceutical compound which is used for the preparation of TAXOL® as an injection solution which is effective in clinical utilization as a cancer-inhibiting drug. The compound comprises dehydrated ethanol, polyepoxilated castor oil, calcium disodium edetate, and tromethamine. Because conventional compounds used as injection solutions are often primarily comprised of dehydrated ethanol and polyepoxilated castor oil, the components which distinguish the present invention with prior art are calcium disodium edetate and tromethamine. Calcium disodium edetate is used as a detoxicant against poisoning from heavy metals, reduces the side effects caused by TAXOL, and prolongs the stability of the solution. Tromethamine (TRIS) is used as an alkalyzer to alleviate breathing difficulties and is also used as a buffering agent for blood plasma.

These together with other objects of the invention are explained clearly in the claims annexed to and forming a part of this disclosure. For a better understanding of the invention, its operating advantages and the specific objects attained by its use, reference should be made to the descriptive matter in which there are disclosed preferred embodiments of the invention.

DETAILED DESCRIPTION OF THE PREFERRED EMBODIMENT

The present invention is a pharmaceutical compound which is used for the preparation of TAXOL® as an injection solution which is effective in clinical utilization as a cancer-inhibiting drug. The addition of calcium disodium edetate and tromethamine to conventional injections solutions enhances the stability of the solution, and reduces the side effects normally associated with administration of TAXOL®. The compound comprises dehydrated ethanol, polyepoxilated castor oil, tromethamine, and calcium disodium edetate in specified ranges. The following are some examples of preparation methods of the enhanced injection solution:

1) 30 mg of tromethamine is added to 10 ml of dehydrated ethanol under the application of heat; the resulting solution is agitated for approximately 5 minutes, and then sonicated for approximately 5 minutes. The solution is brought to room temperature and 300 mg of TAXOL® is added to the solution; the resulting solution is then agitated for approximately 5 minutes and sonicated for approximately 5 minutes. While being agitated, the resulting solution is gradually added to 25 ml of Cremophor EL. A separate solution of 10 mg calcium disodium edetate dissolved in 50 ml of 100% unhydrous ethanol is prepared and agitated for 5 minutes. This solution containing calcium disodium edetate is added to the previous solution until a 50 ml volume is achieved. The resulting solution is agitated for 10 minutes before the final solution is obtained.

2) 60 mg of tromethamine is added to 10 ml of dehydrated ethanol under the application of heat; the resulting solution is agitated for approximately 5 minutes, and then sonicated for approximately 5 minutes. The solution is brought to room temperature and 300 mg of TAXOL® is added to the solution; the resulting solution is then agitated for approximately 5 minutes and sonicated for approximately 5 minutes. While being agitated, the resulting solution is gradually added to 25 ml of Cremophor EL. Hereinafter, this solution will be referred to as solution A. A separate solution, hereinafter referred to as solution B, comprised of 5 mg calcium disodium edetate dissolved in 100% unhydrous ethanol, is prepared and agitated for 5 minutes. Solution B has a volume which would correspond to a total volume of 50 ml when solution B and solution A are mixed. The resulting mixture of solution A and B is agitated for 10 minutes before the final solution is obtained.

3) 20 mg of tromethamine is added to 10 ml of dehydrated ethanol under the application of heat; the resulting solution is agitated for approximately 5 minutes, and then sonicated for approximately 5 minutes. The solution is brought to room temperature and 300 mg of TAXOL® is added to the solution; the resulting solution is then agitated for approximately 5 minutes and sonicated for approximately 5 minutes. While being agitated, the resulting solution is gradually added to 25 ml of Cremophor EL. Hereinafter, this solution will be referred to as solution A. A separate solution, hereinafter referred to as solution B, comprised of 5 mg calcium disodium edetate dissolved in 100% unhydrous ethanol, is prepared and agitated for 5 minutes. Solution B has a volume which would correspond to a total volume of 50 ml when solution B and solution A are mixed. The resulting mixture of solution A and B is agitated for 10 minutes before the final solution is obtained.

The aforementioned examples teach specific amounts of each component which are used to produce different injection solutions. The present invention, however, comprises the use of tromethamine and calcium disodium edetate in injection solutions which have been previously used.

What is claimed as being new and therefore desired to be protected by letters patent by the united states is as follows:

1. A pharmaceutical compound used for the preparation of TAXOL® as an injection solution comprising:

a) TAXOL®;

b) dehydrated ethanol;

c) polyepoxilated castor oil;

d) tromethamine; and e) calcium disodium edetate.

2. A pharmaceutical compound as mentioned in claim 1, wherein the concentration of said tromethamine in solution is between 0.4 and 1.2 mg per ml of solution, the concentration of said calcium disodium edetate in solution is between 0.1 and 0.2 mg per ml of solution.

3. A pharmaceutical compound as mentioned in claim 1, wherein the concentration of said TAXOL® in solution is 6 mg per ml of solution, the concentration of said tromethamine is 0.6 mg per ml of solution, the concentration of said calcium disodium edetate in solution is 0.1 mg per ml of solution, wherein said polyepoxilated castor oil comprises 50% of the total volume of said solution.

* * * * *